United States Patent
Ko et al.

(10) Patent No.: US 8,703,995 B2
(45) Date of Patent: Apr. 22, 2014

(54) METHOD OF PREPARING ALKYL (METH)ACRYLATE

(75) Inventors: Jun-Seok Ko, Daejeon (KR); Hyun-Kyu Kim, Daejeon (KR); Se-Won Baek, Daejeon (KR); Dong-Hyun Cho, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 13/702,533

(22) PCT Filed: Apr. 14, 2011

(86) PCT No.: PCT/KR2011/002671
§ 371 (c)(1),
(2), (4) Date: Dec. 6, 2012

(87) PCT Pub. No.: WO2012/026661
PCT Pub. Date: Mar. 1, 2012

(65) Prior Publication Data
US 2013/0085291 A1    Apr. 4, 2013

(30) Foreign Application Priority Data
Aug. 26, 2010 (KR) .................. 10-2010-0083165

(51) Int. Cl.
*C07C 67/48* (2006.01)
(52) U.S. Cl.
USPC ........................................... 560/248
(58) Field of Classification Search
None
See application file for complete search history.

(56) References Cited

U.S. PATENT DOCUMENTS 5,883,288 A * 3/1999 Iffland et al. .................. 560/205
2010/0029881 A1* 2/2010 Gropp et al. .................. 526/319

FOREIGN PATENT DOCUMENTS

| KR | 10-2011-0009941 |   | 1/2011 |
| WO | 01/19773 | * | 3/2001 |
| WO | WO 2010-058983 |   | 5/2010 |
| WO | WO 01/19773 |   | 3/2011 |

* cited by examiner

*Primary Examiner* — Karl J Puttlitz
(74) *Attorney, Agent, or Firm* — McKenna Long & Aldridge, LLP (57) ABSTRACT

The present invention relates to a method of preparing an alkyl (meth)acrylate, and more specifically to a method of preparing an alkyl (meth)acrylate which comprises the steps of: carrying out an esterification reaction with reactants comprising an alkanol and (meth)acrylic acid in the presence of an organic acid catalyst with a conversion rate of about 70% or more; supplying reaction products of the esterification reaction to a distillation tower equipped with a reboiler at the lower end to purify them; recovering a upper discharge comprising an alkyl (meth)acrylate and water at the upper part of the distillation tower and recovering a lower discharge comprising high boiling materials and water at the lower part of the distillation tower; separating the lower discharge of the distillation tower into a water layer and an organic layer; and recirculating the water layer separated from the lower discharge so as to be used in the esterification reaction, wherein each of the steps occurs continuously and the lower discharge of the distillation tower includes water in an amount of about 2-25% by weight with respect to the total weight of the lower discharge.

34 Claims, 1 Drawing Sheet

METHOD OF PREPARING ALKYL (METH)ACRYLATE

CROSS REFERENCE TO RELATED APPLICATION

This application is a National Stage Entry of International Application No. PCT/KR2011/002671, filed Apr. 14, 2011, and claims the benefit of Korean Application No. 10-2010-0083165, filed on Aug. 26, 2010, which are hereby incorporated by reference in their entirety for all purposes as if fully set forth herein.

TECHNICAL FIELD

The present invention relates to a method of preparing an alkyl (meth)acrylate.

BACKGROUND OF ART

In general, alkyl (meth)acrylates are prepared by esterification reactions of alkanols with acrylic acid in the presence of an acid catalyst. Since the esterification reaction is an equilibrium reaction, eliminating the water as produced out of the reactor shifts the reaction equilibrium in the direction of the forward reaction, increasing conversion rates for the alkyl (meth)acrylates.

Among acid catalysts typically used for the esterification reaction are inorganic acids such as sulfuric acid, organic acids such as alkane sulfonic acids, ion exchange resins and the like.

When sulfuric acid having highly corrosive property is used as a catalyst, it requires for a reactor to have walls finished with anti-corrosive materials and to be of a batch type, rather than a continuous type, for proceeding with the esterification reaction. Also, the catalyst after the completion of the reaction should be removed through neutralization with alkaline materials, requiring large amounts of water and thus incurring additional costs for disposal of wastewater.

When the ion exchange resin is used as a catalyst, its catalytic activity sharply decreases at a temperature of 90° C. or higher so that it is impossible to raise a reaction temperature above 90° C. Accordingly, the reaction should be carried out at a relatively low temperature, causing a lower rate of a reaction and a decreased conversion rate for the overall reaction. As a result, an increased amount of unreacted reactants are recirculated to the reactor so that process efficiency deteriorates. Also, productivity declines as the catalyst should be periodically replaced.

In contrast, when using the organic acid catalyst that is less corrosive than the inorganic acids such as sulfuric acid, one can choose a reactor or a column of various materials. Also, after the reaction, it is possible to continuously proceed with a purification process without any additional treatment with salts.

However, the organic acid catalyst can be a reason for rising production costs since its price is from several to dozens times higher than that of the inorganic acid catalyst. In addition, when being used as catalysts, organic acids can be mixed with high boiling materials, i.e., byproducts of the esterification reaction to form tar-like materials, which can be deposited on a surface of a wall of a reactor or an heat exchanger such as a distillation tower to hinder heat exchange or can cause the clogging of pipes in a decomposition reactor for high boiling materials.

Also, part of the organic acid catalyst is discharged together with heavies as waste oils. Since such an amount of the catalyst as discharged should be replenished in the esterification reactor, it is necessary to minimize the discharged amount of the catalyst. In addition, when the waste oils are incinerated to recover some energy in a form of steam, incineration of the waste oils comprising the organic acid catalyst can cause environmental problems. Therefore, they should be subjected to a pretreatment such as a treatment with salts before incineration and sulfur oxides should be disposed separately after the incineration.

Therefore, in the process for preparing an alkyl (meth)acrylate, a wide variety of studies have been conducted as to methods of increasing a recovering and reusing rate of the organic acid catalyst, and reducing the amount of the organic acid catalyst as finally discarded, but they leave much to be desired.

DETAILED DESCRIPTION OF THE INVENTION

Technical Objectives

The present invention provides a method of preparing an alkyl (meth)acrylate which makes possible during the preparation of the alkyl (meth)acrylate using an organic acid catalyst not only an increase in a recovering and reusing rate of the catalyst but also prevention of a pipe clogging phenomenon in a decomposition reactor for high boiling materials and reduction of the amount of the catalyst as finally discarded.

Technical Solution

In an embodiment, the present invention provides a method of preparing an alkyl (meth)acrylate, which comprises the steps of:

carrying out an esterification reaction with reactants comprising an alkanol and (meth)acrylic acid in the presence of an organic acid catalyst with a conversion rate of about 70% or more;

supplying reaction products of the esterification reaction to a distillation tower equipped with a reboiler at the lower end to purify them;

recovering a upper discharge comprising an alkyl (meth)acrylate and water at the upper part of the distillation tower and recovering a lower discharge comprising high boiling materials and water at the lower part of the distillation tower;

separating the lower discharge of the distillation tower into a water layer and an organic layer; and recirculating the water layer separated from the lower discharge so as to be used in the esterification reaction, wherein each of the steps occurs continuously and the lower discharge of the distillation tower includes water in an amount of about 2-25% by weight with respect to the total weight of the lower discharge.

Also, the method of preparing an alkyl (meth)acrylate further includes a step of supplying water from the upper part of the distillation tower in an amount of about 1.01-1.20 times the weight of the water included in the upper discharge coming out from the upper part of the distillation tower.

In addition, it can be operated under such conditions that the pressure of the upper part of the distillation tower and the temperature of a liquid in the reboiler are at least about 130 Torr but less than 170 Torr and about 65-90° C., respectively; at least about 170 Torr but less than 200 Torr and about 70-95° C., respectively; or at least about 200 Torr but less than 230 Torr and about 75-100° C., respectively.

Also, the method of preparing an alkyl (meth)acrylate can be operated under such conditions that the pressure of the upper part of the distillation tower and the temperature of a liquid in the reboiler are at least about 130 Torr but less than 170 Torr and about 65-90° C., respectively; at least about 170 Torr but less than 200 Torr and about 70-95° C., respectively; or at least about 200 Torr but less than 230 Torr and about 75-100° C., respectively; and can further include a step of supplying water from the upper part of the distillation tower in an amount of about 1.01-1.20 times the weight of the water included in the upper discharge coming out from the upper part of the distillation tower.

Also, the water layer separated from the lower discharge of the distillation tower includes at least 50% by weight of the organic acid catalyst supplied to the esterification reaction.

Also, the preparation method of the present invention further includes a step of supplying the organic layer separated from the lower discharge of the distillation tower to a decomposition reactor for high boiling materials to carry out a decomposition reaction.

The decomposition reaction can proceed at a temperature of about 120-220° C. under a pressure of about 30-760 Torr. Also, the residence time for the decomposition reaction can be, but is not limited to, 1-40 hours in light of a supply rate of the reactants or the like.

Also, the preparation method of the present invention can further include a step of supplying a portion of the water layer separated from the lower discharge of the distillation tower into the decomposition reactor for high boiling materials. In this step, the catalyst contained in the decomposition reactor can be included in an amount of about 0.01-5% by weight with respect to the total weight of the reacting liquids fed into the decomposition reactor.

Also, the preparation method of the present invention can further include a step of recirculating the upper discharge of the decomposition reactor to the step of the esterification reaction. In addition, it can further include a step of recirculating the upper discharge of the decomposition reactor to the step of purifying the reaction products of the esterification reaction.

Also, the catalyst included in the lower discharge of the decomposition reactor for high boiling materials can be in an amount of at most 10% by weight with respect to the total weight of the lower discharge.

In addition, the esterification reaction can proceed in one or more continuous type reactor(s) connected in series and a water separation tower can be further included for purifying the water discharged from the upper part of each of the continuous type reactors.

Also, the esterification reaction can proceed at a temperature of about 70-150° C. under a pressure of about 50-760 Torr.

In the step of the esterification reaction, a molar ratio of the alkanol to (meth)acrylic acid included in the reactants can be about 1-5.

Also, in the step of the esterification reaction, the content of the organic acid catalyst can be about 0.01-5% by weight with respect to the total weight of the reactants.

In addition, the alkanol can be an alkanol having from 4 to 8 carbon atoms.

Also, the organic acid catalyst can be at least one selected from the group consisting of alkane sulfonic acids and aryl sulfonic acids.

MODE FOR PRACTICING THE INVENTION

Hereinafter, the method of preparing an alkyl (meth)acrylate in accordance with the embodiments of the present invention will be explained.

Before that, unless it is explicitly mentioned in the entire specification, the term "(meth)acrylic acid" is defined to collectively denote acrylic or methacrylic acid; the term "alkyl (meth)acylate" is defined to collectively denote an alkyl acrylate or an alkyl methacrylate.

Also, the term "reactant" is defined to include a mixture of (meth)acrylic acid and alkanols for the esterification reaction; the term "conversion rate" means a ratio in percentage terms of the reacted amount to the supplied amount of the limiting reactant among the reactants.

And, the term "reacted product" is defined to include not only the alkyl (meth)acrylate produced after the esterification reaction but also adducts, unreacted reactants, the catalysts, and the like.

Also, the term "high boiling materials" collectively denotes Michael adducts that are generated from Michael reaction (i.e., Michael addition) either between the reactant and the product or between the reactants and have a boiling point higher than that of a target alkyl (meth)acrylate.

Also, the term "heavies" means a mixture of high boiling materials, the catalysts used in the preparation process of an alkyl (meth)acrylate, polymerization inhibitors, other polymers, and the like.

During a series of researches into the preparation method of an alkyl (meth)acrylate, the present inventors have found the followings and completed the present invention: The content of the water included in the lower discharge of the distillation tower can be controlled within a specific range when the amount of the water in the refluxed liquid fed into the upper part of the distillation tower is supplied to be more than that of the water recovered from the upper part of the distillation tower by using the phenomenon that the alkyl (meth)acrylate forms an azeotrope with alkanols and water in the step of supplying the esterification products to the distillation tower to purify them, when in the purification step the temperature of the liquid in the reboiler of the distillation tower depending on the pressure range in the distillation tower is controlled within a specified range, or when the aforementioned two conditions are satisfied at the same time. As a result, the lower discharge can be easily separated into a water layer and an organic layer so that the organic acid catalyst contained in the water layer can be effectively recovered and thus the amount of the discarded catalyst can be minimized. Also, it is possible to ensure the fluidity in the decomposition reactor for high boiling materials and thus prevent the clogging of piping.

According to an embodiment, the present invention provides a method of preparing an alkyl (meth)acrylate which comprises the steps of:

carrying out an esterification reaction with reactants comprising an alkanol and (meth)acrylic acid in the presence of an organic acid catalyst with a conversion rate of about 70% or more;

supplying reaction products of the esterification reaction to a distillation tower equipped with a reboiler at the lower end to purify them;

recovering a upper discharge comprising an alkyl (meth)acrylate and water at the upper part of the distillation tower and recovering a lower discharge comprising high boiling materials and water at the lower part of the distillation tower;

separating the lower discharge of the distillation tower into a water layer and an organic layer; and recirculating the water layer separated from the lower discharge so as to be used in the esterification reaction, wherein each of the steps occurs continuously and the lower discharge of the distillation tower includes water in an amount of about 2-25% by weight with respect to the total weight of the lower discharge.

Hereinafter, each of the steps that can be included in the method of preparing an alkyl (meth)acrylate in accordance with the present invention will be explained in more detail.

First, the method of preparing an alkyl (meth)acrylate according to the present invention includes a step of carrying out an esterification reaction with reactants comprising (meth)acrylic acid and alkanols in the presence of an organic acid catalyst (hereinafter, as referred to as "the step of the esterificaiton reaction").

The step of the esterification reaction is a step of proceeding esterification with reactants of (meth)acrylic acid and alkanols and can be carried out in the presence of an organic acid catalyst. Reaction products from this step mainly includes the alkyl (meth)acrylate (i.e., the desired product) and water (i.e., a byproduct), besides which unreacted reactants and products from side reactions can be included.

In the present invention, the step of the esterification reaction can be carried out in conventional apparatus under typical conditions in the art of the present invention, except that the conversion rate for the limiting reactant among the reactants should be made at least about 70%.

The conversion rate can be defined as the following Formula 1. The conversion rate can be made at least about 70%, preferably at least about 90%, and more preferably about 95-99.9% in order to generate the alkyl (meth)acrylate as much as possible through the esterification reaction and thereby achieve a higher productivity. The conversion rate can be determined by using conventional methods such as gas chromatography or the like.

[Formula 1]
$$\text{conversion rate (\%)} = \frac{\text{a total weight of the limiting reactant as consumed}}{\text{a total weight of the limiting reactant as introduced}} \times 100$$

For the (meth)acrylic acid among the reactants, one can use the one typically used in the art to which the present invention pertains without particular limitation.

Also, one can properly select and use an alkanol as a reactant depending on the target (meth)acrylate without particular limitation, however, preference is given to using alkanols having from 4 to 8 carbon atoms. More preferably, the alkanol can be at least one selected from the group consisting of n-butanol, i-butanol, t-butanol, n-pentanol, t-amylalcohol, n-hexanol, n-heptanol, n-octanol and 2-ethylhexyl alcohol.

In the esterification reactor, a ratio between the (meth) acrylate and the alkanol as included in the reactants can be determined in various ranges, in light of reaction efficiency. Preferably, with respect to 1 mole of (meth)acrylic acid, the amount of the alkanol can be about 1-5 moles, preferably about 1.05-3 moles, and more preferably about 1.1-2.5 moles. In this case, the reaction ratio between the (meth)acrylic acid and the alkanol is a ratio calculated with comprising not only fresh feed as supplied into the reactor but also the (meth) acrylic acid and the alkanol as recirculated and supplied again after reaction, and it means a molar ratio between the reactants in the esterification reactor.

As the esterification reaction of alkanols with (meth) acrylic acid is a equilibrium reaction, it is advantageous for the continuous production of the (meth)acrylate that in the continuous preparation process, starting materials, i.e., (meth)acrylic acid and alkanols are supplied in excess amounts with water being continuously eliminated from the reaction products.

Also, for the organic acid catalyst used in this step, one can use any typical organic acid catalyst available for the esterificatiion reaction in the art to which the present invention pertains. Preference is given to using at least one selected from the group consisting of alkane sulfonic acids and aryl sulfonic acids. More preferably, the organic acid catalyst is at least one selected from the group consisting of methane sulfonic acid, benzene sulfonic acid, p-toluene sulfonic acid, and straight chain type alkyl benzene sulfonic acids.

The content of the organic acid catalyst can be properly determined depending on the types of the reactants or the catalyst to be used, but it can be about 0.01-5% by weight, preferably about 0.01-3% by weight, and more preferably about 0.01-2.5% by weight, with respect to the reactant.

Also, a polymerization inhibitor can be used for the purpose of preventing polymerization between the (meth)acrylic acid (i.e., the reactant) and the alkyl (meth) acrylate (i.e., the product). In this regard, one can use any polymerization inhibitor having an effect of preventing polymerization of the (meth)acrylic acid and the alkyl (meth) acrylate without any particular limitation. Preferably, the polymerization inhibitor can be a phenol compound comprising hydroquinone, p-methoxy phenol, or the like; an amine compound comprising phenothiazine, N-phenyl-N'-isopropyl p-phenylenediamine, N,N'-di-2-naphtyl p-phenylenediamine, N-phenyl-N'-(1,3-dimethylbutyl) p-phenylenediamine, or the like; or N-oxyl compound comprising 4-hydroxy-2,2,6,6-tetramethyl piperidine-N-oxyl, 4-benzoyloxy-2,2,6,6-tetramethyl piperidine-N-oxyl, 4-acetylamino-2,2,6,6-tetramethyl piperidine-N-oxyl, or the like.

The content of the polymerization inhibitor can be properly determined depending on the types of the reactant or the polymerization inhibitor to be used, but it can be about 0.01-1% by weight, preferably about 0.05-0.5% by weight, and more preferably about 0.05-0.45% by weight with respect to the total weight of the alkyl (meth)acrylate as prepared.

Also, the esterification reaction can be carried out under the conditions typically applied in the art to which the present invention pertains. For a more efficient reaction, the reaction can be carried out at a temperature of about 70-150° C., preferably about 70-130° C., and more preferably about 80-120° C. Also, the reaction pressure of the esterification can be determined to be a pressure under which the water as produced can be continuously eliminated at each of the reaction temperatures, ranging from about 50 Torr to about 760 Torr, preferably from about 50 Torr to about 700 Torr, and more preferably from about 100 Torr to about 600 Torr.

As a reactor for carrying out the step of the esterification reaction, one can use a continuous stirred-tank reactor typically used in the art to which the present invention pertains, in light of production efficiency. Also, for efficient management of the process, at least one of such continuous type reactors can be connected in series. In addition, for the purpose of shifting the reaction equilibrium in the desired direction by removal of the water produced as a byproduct in the esterification reaction, it is preferable to eliminate the water via the upper part of each of the continuous type reactors, and a water separator can be fitted to the upper part of the reactor.

Figure 1:
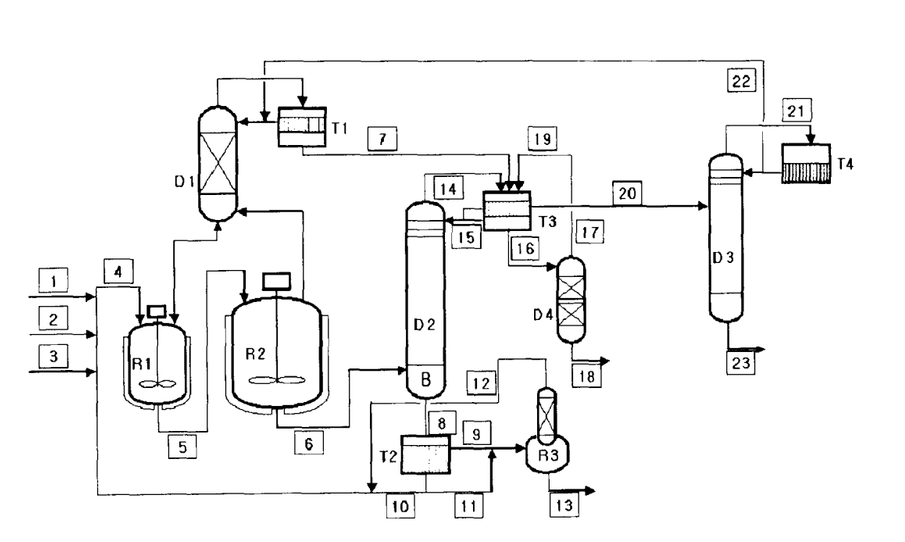
FIG. 1 is a process flow diagram schematically illustrating a process for preparing an alkyl (meth)acrylate in accordance with an embodiment of the present invention.

FIG. 1 is a process flow diagram schematically illustrating the process for preparing an alkyl (meth)acrylate in accordance with an embodiment of the present invention. In a example of the step of esterification reaction, referring to FIG. 1, the esterification reaction can proceed in two continuous type reactors, R1 and R2 that are connected in series.

Among them, a first reactor R1 is a pre-reactor, into which (meth)acrylic acid, an alkanol and a catalyst can be fed continuously via a first flow 1, a second flow 2, and a third flows 3. The pre-reaction can proceed with the residence time of the reactants ranging from about 0.1 to 2 hours to have a conversion rate of the limiting reactant between about 20% and about 80%. Also, in a second reactor R2 subsequent to the first reactor R1, the esterification reaction can proceed with the residence time of the reactant ranging from about 1 to 3 hours to have a conversion rate of the limiting reactant of about 70% or more, preferably about 90% or more, and more preferably between about 95% and about 99.9%.

In this step, water can be removed via the upper part of each of the continuous type reactors, R1 and R2. At the upper part of a water separation tower D, the water, the alkanol, and the alkyl (meth)acrylate can form an azeotrope together to come out as an upper discharge, which is then separated into a water layer and an organic layer at a decanter and receiver T1. The water layer can include some of the alkanol. The organic layer can be recirculated into the first reactor R1 and the water layer can be recovered with a decanter and receiver T3 connected to a distillation tower D2 of a purification step that will be explained below and then it can be used as a refluxed liquid at the purification step.

However, the present invention is not limited to the embodiment illustrated by FIG. 1 as explained above. In the continuous reactor connected in series as such, the present invention can be designed in various manners by controlling a reaction temperature, the types and the amount of the catalyst, the residence time of the reactants and the reaction products (or the volume of the reactor), the types of the reactor or the like in order to control the conversion rate of the limiting reactant and thus optimize the reaction process.

In the preparation method of the present invention, the step of the esterification reaction can be followed by a step of supplying reaction products of the esterification reaction to a distillation tower to purify them (hereinafter, referred to as the purification step).

The purification step is a step for separating the alkyl (meth)acrylate (i.e., a target product) from the reaction products of the aforementioned step for the esterification reaction by distillation.

In the purification step, one can use distillation towers typically used in the art to which the present invention pertains. The distillation tower can be preferably equipped with a reboiler at its lower end, and types of the reboiler can be a typical one in the art of the present invention, such as a Kettle type, a Shell and Tube type, or the like. Also, the distillation tower can use packing columns filled with fillers such as pallings, rashing ring, structured packing, or the like, columns of tray types such as a older show or a lift tray, downcomer type columns or the like. Also, the theoretical number of the trays in the distillation tower is preferably at least 20 in light of a separation capacity and efficiency but at most 60 in light of holding a differential pressure at a low level.

In particular, according to the present invention, in a recovery step continuously following the purification step, the amount of the water included in the lower discharge of the distillation tower should be in the range specified in accordance with the present invention, which can be achieved by (i) controlling the amount of water added to the refluxed liquid in the purification step; (ii) regulating a supplied heat of the reboiler fitted to the lower part of the distillation tower to control the temperature of the liquid in the reboiler within a specified range depending on the pressure range of the upper part of the distillation tower; or (iii) satisfying both the foregoing conditions at the same time.

Specifically, (i) controlling the amount of water added to the refluxed liquid in the purification step can be carried out by further comprising a step of supplying water from the upper part of the distillation tower in an amount of about 1.01-1.20 times the weight of the water contained in the discharge coming out from the upper part of the distillation tower. The amount of the water supplied from the upper part of the distillation tower can be about 1.01-1.20 times, preferably about 1.01-1.15 times, and more preferably about 1.01-1.10 times the weight of the water contained in the upper discharge coming out from the upper part of the distillation tower.

In the purification step, the water, the alkanol and the alkyl (meth)acrylate form an azeotrope with a certain composition under the operating pressure to be discharged from the upper part of the distillation tower and the flow rate of the water can be determined by the flow rate of the discharge from the upper part of the distillation tower. From the total amount discharged from the upper part of the distillation tower, the amount of the water added to the refluxed liquid can be controlled so as to be within the aforementioned range. For example, if the water content in the azeotropic composition of the upper part of the distillation tower is about 40% by weight, the amount of water added to the refluxed liquid can be controlled so as to be about 40.4-48% by weight of the total flow rate of the discharge from the upper part of the tower.

Also, (ii) controlling the temperature of the liquid in the reboiler depending on the pressure range of the upper part of the distillation tower can be carried out by operating the purification step under such conditions that the pressure of the upper part of the distillation tower and the temperature of the liquid in the reboiler can be at least about 130 Torr but less than about 170 Torr and about 65-90° C., respectively; at least about 170 Torr but less than about 200 Torr and about 70-95° C., respectively; or at least about 200 Torr but less than 230 Torr and about 75-100° C., respectively.

Also, (iii) the amount of the water added to the refluxed liquid can be controlled within the range as described above and at the same time the temperature of the liquid in the reboiler can be controlled within the range as stated above depending on the pressure range of the upper part of the distillation tower. In other words, the process can be operated under such conditions that the pressure of the upper part of the distillation tower and the temperature of the liquid in the reboiler is at least about 130 Torr but less than about 170 Torr and about 65-90° C., respectively; at least about 170 Torr but less than about 200 Torr and about 70-95° C., respectively; or at least about 200 Torr but less than 230 Torr and about 75-100° C., respectively; while water is supplied from the upper part of the distillation tower in an amount of about 1.01-1.20 times, preferably about 1.01-1.15 times, and more preferably about 1.01-1.10 times the weight of the water contained in the upper discharge coming out from the upper part of the distillation tower.

As such, through the above procedures, the content of the water included in the lower discharge of the distillation tower can be controlled within the range according to the present invention so that the lower discharge of the distillation tower can be separated into a water layer and an organic layer, thereby accomplishing the objectives of the present invention. This will be described as below.

An embodiment of the purification step is now explained with reference to FIG. 1. The reaction products prepared from the esterification reaction as described above are supplied to the distillation tower D2 and the reaction products as supplied stay for a certain period of time in the reboiler fitted to the lower part of the distillation tower to be distilled. At this time, the refluxed liquid comprising water can be supplied to the upper part of the distillation tower D2 via the decanter and receiver T3, however, the present invention is not limited to the foregoing example.

In the preparation method of the present invention, the purification step can be followed by a step of recovering the upper discharge comprising the alkyl (meth)acrylate, the alkanol, and the water at the upper part of the distillation tower and recovering the lower discharge comprising heavies such as high boiling materials and the like, the (meth) acrylic acid, the alkanol, the akyl (meth) acrylate, and water at the lower part of the distillation tower.

The alkyl (meth)acrylate is typically recovered from the upper part of the distillation tower as constituent of an azeotrope comprising water and alkanols. For the purpose of recovering the alkyl (meth)acrylate from the upper part of the distillation tower, alkanols and water can be additionally introduced as a refluxed liquid.

Each of the alkyl (meth)acrylate, the alkanol and the water that are recovered from the upper part of the distillation tower in the purification step can be separated through an additional distillation apparatus, and thereby a highly pure alkyl (meth) acrylate can be obtained. The water and the alkanols as separated can be recirculated into the step of the esterification reaction or the purification step.

Also, in the purification step, the unreacted (meth) acrylic acid, the organic acid catalyst, the polymerizaton inhibitor, water and the high boiling materials, which are mixed together, are mainly recovered from the lower part of the distillation tower, and the alkyl (meth)acrylate and the alkanol that fail to be discharged from the upper part of the distillation tower are possibly included therein. The lower discharge of the distillation tower is recirculated again to the step of the esterification reaction.

As defined above, the high boiling materials are mainly Michael adducts generated from the Michael reaction (i.e., Michael addition) between the reactant and the product or between the reactants and have a higher molecular weight and a higher boiling point than those of the alkyl (meth)acrylate. After being decomposed at a high temperature in the presence of an acid catalyst, they can be reused as decomposition products. Representative examples of the high boiling materials possibly generated from the method of preparing butyl methacrylate among the alkyl (meth)acrylates include β-butoxypropionic acid ($C_4H_9OCH_2CH_2COOH$), n-butyl diacrylate, ($CH_2CHCOOCH_2CH_2COOC_4H_9$), butyl-β-butoxypropionate ($C_4H_9OCH_2CH_2COOC_4H_9$) and the like.

In particular, according to the present invention, it is advantageous that the content of the water included in the lower discharge of the distillation tower should be maintained at about 2-25% by weight, preferably about 3-20% by weight, and more preferably about 3-15% by weight with respect to the total weight of the lower discharge. If the content of the water included in the lower discharge of the distillation tower is within the aforementioned range, the lower discharge of the distillation tower can be separated into a water layer and an organic layer in a subsequent step and thereby the organic acid catalyst used in the reaction can be easily recovered. Details of this process will be discussed afterwards.

In the preparation method according to the present invention, the recovering step can be sequentially followed by separating the lower discharge of the distillation tower into a water layer and an organic layer; and recirculating the water layer separated from the lower discharge so as to be used in the esterification reaction.

The lower discharge of the distillation tower includes heavies such as high boiling materials, the catalyst, the polymerization inhibitor, and the like. Recirculating the lower discharge into the esterification reaction as it is can cause a problem that the heavies are accumulated and thus depositied in the reactor or the heat exchanger or pipings of the distillation tower. Therefore, a certain amount of the heavies should be discharged out of the system so as to prevent such accumulation.

Conventional methods of preparing the alkyl (meth)acrylate typically include a separate step of taking out some of the lower discharge of the distillation tower and cracking the high boiling materials among the heavies. When being subjected to hydrolysis or a thermal decomposition in the presence of the organic acid catalyst, the high boiling materials can be recovered as (meth) acrylic acid, the alkanol or the alkyl (meth)acrylate.

In the process of decomposing the high boiling materials, the organic acid catalyst is discharged and disposed as waste oils together with the heavies, and the esterification reactor should be replenished with such an amount of the organic acid catalyst as discharged. Furthermore, disposal of the waste oils comprising a large amount of the organic acid catalyst can cause serious environmental problems. Therefore, the discharged amount of the catalyst should be minimized but at the same time, the minimum amount of the catalyst required for the decomposition of the high boiling materials should be maintained.

In conventional methods of preparing an alkyl (meth)acrylate, however, a large amount of the catalyst is discharged together with the waste oils so that the expensive organic acid catalyst is consumed in great quantities and thereby production efficiency deteriorates.

In light of this, the present inventors has found the followings to reach the present invention: In the step of supplying the reaction products of the esterification to the distillation tower to purify them, (i) controlling the amount of the water added to the refluxed liquid for the purpose of discharging the alkyl amount of the catalyst is not sufficient, leading to an increase in the amount of the catalyst discarded in the decomposition reactor for high boiling materials. For example, when the amount of water included in the lower discharge of the distillation tower is less than 2% by weight with respect to the total weight of the lower discharge and p-toluene sulfonic acid is used as the organic acid catalyst, it is impossible to separate the lower discharge into the water layer and the organic layer. Also, although the lower discharge can be separated by using methane sulfonic acid or benzene sulfonic acid as the organic acid catalyst in the aforementioned case, the amount of the catalyst contained in the water layer is less than 50% by weight of the catalyst supplied into the esterification reaction, which is insufficient for a recovered amount of the catalyst.

Also, in the case of supplying a refluxed water into the upper part of the distillation tower in excess amount or lowering the temperature of the liquid in the reboiler depending on the pressure range of the upper part of the distillation tower more than needs, the water content in the lower discharge of the distillation tower become so high that the amount of the water to be treated in the reactor increases, causing an increase in energy costs and a decrease in the reaction rate. Therefore, it is preferable that the content of the water contained in the lower discharge of the distillation tower is at most about 25% by weight with respect to the total weight of the lower discharge.

As described above, controlling the amount of water included in the lower discharge of the distillation tower allows the lower discharge to be separated into the water layer and the organic layer, and the water layer as separated includes the major amount of the organic acid catalyst used in the esterification reaction. Among the specific examples of the organic acid catalyst, methane sulfonic acid and benzene sulfonic acid are known to have a infinitely high solubility in water, and as a different example, p-toluene sulfonic acid has a high solubility, i.e., 67g per 100 ml of water, and thus they can be easily dissolved in the water layer separated from the lower discharge of the distillation tower. Also, since the organic acid catalyst has a relatively high specific gravity as compared with the lower discharge of the distillation tower, most of the catalyst can be dissolved well in the water layer even with a short residence time.

The water layer thus separated from the lower discharge of the distillation tower can include at least about 50%, preferably at least about 60%, and more preferably about 70-99% by weight of the organic acid catalyst supplied to the esterification reaction. As illustrated in FIG. 1, the step of separating the lower discharge of the distillation tower into the water layer and the organic layer can be carried out in a separate decanter and receiver T2, and the water layer separated therefrom can be recirculated into the esterification reaction (See flow 10). As a result, in the preparation method of the present invention, the organic acid catalyst can be easily recovered prior to the decomposition reaction of the high boiling materials that will be described afterwards so that the amount of the discarded catalyst can be minimized, and reusing the organic acid catalyst can reduce problems arising in the disposal of the catalyst. Also, the clogging phenomenon of the piping due to a generated slurry can be alleviated so that stable operations of the process can be achieved.

The preparation method of the present invention can further include a step of supplying the organic layer separated from the lower discharge of the distillation tower into a decomposition reactor for high boiling materials to carry out a decomposition reaction.

The organic layer separated from the lower discharge of the distillation tower includes most of high boiling materials, which can be subjected to hydrolysis or a thermal decomposition in the presence of the organic acid catalyst in an additional decomposition reactor to be recovered as an alkyl (meth)acrylate, an alkanol, and (meth)acylic acid. Undecomposed high boiling materials and heavies such as the polymerization inhibitor and the organic acid catalyst can be discharged and discarded.

All of the organic layer separated from the lower discharge of the distillation tower can be supplied into the decomposition reactor. Alternatively, in light of the efficiency of the continuous process, about 5-50% by weight, preferably about 5-40% by weight, and more preferably about 5-30% by weight of the organic layer can be supplied into the decomposition reactor for high boiling materials to carry out the decomposition reaction with the rest of it being recirculated to the step of the esterification reaction.

The decomposition reaction of high boiling materials can be carried out at a temperature of about 120-220° C., preferably about 120-200° C., and more preferably about 120-180° C. for a residence time of about 1-40 hours, preferably about 2-30 hours, and more preferably about 3-20 hours, taking the efficiency of the decomposition reaction into account.

The pressure of the decomposition reactor for high boiling materials, which is varied with a temperature, is maintained to be a pressure under which the decomposition products, i,e., the (meth) acrylic acid, the alkanol, and the alkyl (meth) acrylate can be recovered at the upper part of the reactor. It can be determined in the range of 30-760 Torr, preferably about 50-700 Torr, and more preferably about 50-600 Torr.

Also, the decomposition reaction of the high boiling materials can be facilitated by the presence of the acid catalyst. Therefore, the preparation method of the present invention can further include a step of supplying a portion of the water layer separated from the lower discharge of the distillation tower into the decomposition reactor for high boiling materials.

Since the water layer separated from the lower discharge of the distillation tower includes a large amount of the organic acid catalyst, supplying the water layer into the decomposition reactor for high boiling materials can facilitate the decomposition reaction for the heavies.

By maintaining the amount of the catalyst included in the decomposition reactor for high boiling materials at about 0.01-5% by weight, preferably about 0.05-3% by weight, and more preferably about 0.1-2% by weight with respect to the total weight of the reaction liquid supplied into the decomposition reactor (i.e., the total weight of the organic layer supplied into the decomposition reactor for high boiling materials), it is possible to accelerate the decomposition reaction of the high boiling materials and to prevent the clogging phenomenon of the piping by ensuring the fluidity in the decomposition reactor, with the amount of the catalyst to be discarded being minimized.

For supplying part of the water layer separated from the lower discharge of the distillation tower into the decomposition reactor for high boiling materials, one can supply either continuously or intermittently the water layer so as to have a concentration of the organic acid catalyst within the range as described above.

After the step of the decomposition reaction of the high boiling materials, the upper discharge of the decomposition reactor can include the alkyl (meth)acrylate, the alkanol, and the (meth)acrylic acid derived from the decomposition of the high boiling materials, which can be recirculated into the step of esterification reaction or the purification step for the reaction product of the esterification.

That is, the preparation method of the present invention can further include a step of recirculating the upper discharge of the decomposition reactor into the step of the esterification reaction. Also, it can further includes a step of recirculating the upper discharge of the decomposition reactor into the purification step for the reaction products of the esterification.

In the lower discharge of the decomposition reactor, undecomposed heavies such as a tar component and the like and the organic acid catalyst can be in a mixed state.

In conventional methods of preparing an alkyl (meth)acrylate, the amount of the catalyst that is contained in the lower discharge of the decomposition reactor and thus discarded is so large that a lot of the expensive organic acid catalyst is consumed and the production efficiency deteriorates. Also, the process for discarding the waste oils containing a large amount of the organic acid catalyst brings about serious environmental problems.

In contrast, as stated above, the preparation method of the present invention have advantages that most of the organic acid catalyst can be effectively recovered prior to the step of decomposing the high boiling materials and thus the amount of the catalyst to be discarded can be minimized. In the preparation method of the present invention, the lower discharge of the decomposition reactor for high boiling materials advantageously includes the catalyst in an amount of at most about 10% by weight, preferably at most about 5% by weight, and more preferably about 1-5% by weight.

According to an embodiment of the present invention, in the step of decomposition reaction of high boiling materials, as illustrated in FIG. 1, the organic layer separated from the decanter and receiver T2 is supplied to the decomposition reactor for high boiling materials R3 and the upper discharge of the decomposition reactor R3 can be either recirculated into the esterification reactor R1 (see Flow 12) or recirculated into the distillation tower D2 (no corresponding flow is shown in FIG. 1). For accelerating the decomposition reaction, some of the water layer separated from the decanter and receiver T2 can be supplied into the decomposition reactor R3. Also, the lower discharge of the decomposition reactor R3 can be discarded as waste oils (See Flow 13).

As such, the method of preparing an alkyl (meth)acrylate according to the present invention includes the steps of carrying out an esterification reaction with reactants comprising an alkanol and (meth)acrylic acid in the presence of an organic acid catalyst with a conversion rate of about 70% or more; supplying reaction products of the esterification reaction to a distillation tower equipped with a reboiler at the lower end to purify them; recovering a upper discharge comprising an alkyl (meth)acrylate and water at the upper part of the distillation tower and recovering a lower discharge comprising high boiling materials and water at the lower part of the distillation tower; separating the lower discharge of the distillation tower into a water layer and an organic layer; and recirculating the water layer separated from the lower discharge so as to be used in the esterification reaction, wherein each of the steps occurs continuously and the water included in the lower discharge of the distillation tower is maintained at an amount of about 2-25% by weight with respect to the total weight of the lower discharge.

However, besides the aforementioned steps, the preparation method of the present invention can further includes any step typically carried out in the art to which the present invention pertains before or after each of the aforementioned steps and the present invention is not limited by the steps as described above.

Hereinafter, preferred examples will be presented for a better understanding of the present invention. However, the following examples are merely illustrative of the present invention and not intended to limit the present invention.

Although a method of preparing butyl acrylate is explained in the following examples, the preparation method of the present invention is not limited thereto. The same process can be applied for preparing an alkyl (meth)acrylate prepared by the esterification reaction with (meth)acrylic acid and alkanols of 4 to 8 carbon atoms.

COMPARATIVE EXAMPLE 1

Butyl acrylate was prepared as a target alkyl (meth)acrylate.

For this, acrylic acid and n-butanol were used as starting materials, and p-toluene sulfonic acid and phenothiazine were used for a catalyst and a polymerization inhibitor, respectively.

Reactors, each having a volume of 2.5 L and a capacity of 5 L, were installed in series and used as an esterification reactor, and a tray column of 40 tray downcomer type was used as a distillation tower for the purification step. A thermosyphon type reboiler with a capacity of 400 mL was used as fitted to the lower end of the distillation tower. Also, a double jacket type reactor with a capacity of 300 mL was used as a decomposition reactor for high boiling materials with the volume of the liquid being maintained at 200 mL.

346 g/hr of acrylic acid and 359 g/hr of n-butanol were fed into a first reactor R1 among the esterification reactors respectively. As an organic acid catalyst, p-toluene sulfonic acid was dissolved in n-butanol and continuously fed into the first reactor R1 with a flow rate of 3.0 g/hr. A mixed liquid comprising n-butanol, butyl acrylate, and water with the ratio of 7 (n-butanol):2 (butyl acrylate):1 (water) that was recircualted after an additional purification of the organic layer recovered from the upper part of the distillation tower in the purification step was fed into the upper part of a water separation tower D1 with a flow rate of 191 g/hr.

The esterification reaction proceeded such that the residence time of the reactants, the reaction temperature, and the reaction pressure in the first reactor R1 of the esterification reactors were 1.4 hours, 95° C. and 330 Torr, respectively; and the residence time of the reactants, the reaction temperature, and the reaction pressure in a second reactor R2 of the esterification reactors were 2.9 hours, 103° C. and 330 Torr, respectively. The content of the catalyst in the second reactor R2 was 1.01% by weight.

Subsequently, the reaction liquid discharged from the second reactor R2 of the esterification reactors was fed into the bottom of the distillation tower D2 wherein the pressure and the temperature of the upper part of the distillation tower D2 were 150 Torr and 54° C., respectively and the temperature of the liquid in the reboiler fitted to the lower end of the distillation tower was controlled to be 92° C.

Also, a refluxed liquid comprising 96.5% by weight of water and 3.5% by weight of n-butanol was fed into the upper part of the distillation tower D2 with a flow rate of 540 g/hr and at the same time, butyl acrylate with 1.5% by weight of phenothiazine was fed with a flow rate of 22 g/hr.

Meanwhile, the upper discharge of the distillation tower D2 came out at a flow rate of 1319 g/hr and the lower discharge of the distillation tower D2 came out at a flow rate of 742 g/hr. The composition of the upper discharge of the distillation tower D2 was 48.5 (butyl acrylate):39.5 (water):12.0 (n-butanol) with acrylic acid being less then 1 ppm. In other words, the amount of the water supplied from the upper part of the distillation tower D2 (converted value: 521.1 g/hr) was maintained to be approximately equal to (i.e., 1.00 times) the amount of the water recovered from the upper part of the distillation tower in the recovery step (converted value: 521.005 g/hr)

Also, the lower discharge of the distillation tower contained less than 1% by weight of water, 2.5% by weight of acrylic acid, 7.4% by weight of n-butanol, and 57% by weight of butyl acrylate with the rest being heavies such as high boiling materials, the polymerization inhibitor, the catalyst and the like.

The lower discharge of the distillation tower D2 failed to be separated into a water layer and an organic layer, and some (148 g/hr) of the lower discharge was fed into a decomposition reactor for high boiling materials R3 while the rest of it was recirculated into the first esterification reactor R1.

The residence time in the decomposition reactor for high boiling materials R3 was 7.5 hours and the decomposition reaction proceeded at a temperature of 157° C. under a pressure of 100 Torr. The upper discharge of the decomposition reactor R3 came out at a flow rate of 122 g/hr and then it was recirculated into the first esterification reactor R1. Also, the lower discharge of the decomposition reactor for heavies R3 came out at a flow rate of 26.5 g/hr and the content of the organic acid catalyst therein was 11.5% by weight with respect to the total weight of the lower discharge.

When the process was operated for about 70 hours under such conditions as stated above, solid slurry was deposited in the decomposition reactor for high boiling materials R3 so that further operation became impossible to carry out.

EXAMPLE 1

Butyl acrylate was prepared as a target alkyl (meth)acrylate.

For this, acrylic acid and n-butanol were used as starting materials, and methane sulfonic acid and phenothiazine were used for a catalyst and a polymerization inhibitor, respectively. Also, for each of an esterification reactor and a distillation tower, a reboiler of the distillation tower, and a decomposition reactor for high boiling materials, the same apparatus was used as in Comparative Example 1.

First, 347 g/hr of acrylic acid and 360 g/hr of n-butanol were fed into a first reactor R1 of the esterification reactors, respectively. As an organic acid catalyst, 0.7 g/hr of methane sulfonic acid dissolved in n-butanol was continuously introduced. (In Example 1, an increased amount of the catalyst could be recovered and thus the amount of the discarded catalyst decreased so that in comparison with Comparative Example 1, the amount of the catalyst to be replenished was able to decrease) A mixed liquid comprising n-butanol, butyl acrylate, and water with the ratio of 7 (n-butanol):2 (butyl acrylate):1 (water) that was recircualted after an additional purification of the organic layer recovered from the upper part of the distillation tower in the purification step was fed into the upper part of a water separation tower D1 with a flow rate of 191 g/hr.

The esterification reaction proceeded such that the residence time of the reactants, the reaction temperature, and the reaction pressure in the first reactor R1 of the esterification reactors were 1.41 hours, 95° C. and 330 Torr, respectively; and the residence time of the reactants, the reaction temperature, and the reaction pressure in a second reactor R2 of the esterification reactors were 2.9 hours, 103° C. and 330 Torr, respectively. The content of the catalyst in the second reactor R2 was 0.96% by weight.

Subsequently, the reaction liquid discharged from the second reactor R2 of the esterification reactors was introduced into the bottom of the distillation tower D2 wherein the pressure and the temperature of the upper part of the distillation tower D2 were 150 Torr and 54° C., respectively and the temperature of the liquid in the reboiler fitted to the lower end of the distillation tower was controlled to be 83° C.

Also, a refluxed liquid comprising 96.5% by weight of water and 3.5% by weight of n-butanol was fed into the upper part of the distillation tower D2 at a flow rate of 561 g/hr and at the same time, butyl acrylate with 1.5% by weight of phenothiazine was introduced at a flow rate of 22 g/hr.

Meanwhile, 1323 g/hr of the upper discharge and 761 g/hr of the lower discharge flowed out from the distillation tower. The composition of the upper discharge of the distillation tower D2 was 48.5 (butyl acrylate):39.5 (water):12.0 (n-butanol) with acrylic acid being less then 1 ppm. In other words, the amount of the water supplied from the upper part of the distillation tower D2 (the converted value: 543.365 g/hr) was maintained to be about 1.04 times the amount of the water recovered from the upper part of the distillation tower in the recovery step (converted value: 522.585 g/hr).

Also, the lower discharge of the distillation tower D2 contained 4.8% by weight of water, 2.4% by weight of acrylic acid, 7.2% by weight of n-butanol, and 57% by weight of butyl acrylate with the rest being heavies such as high boiling materials, the polymerization inhibitor, the catalyst and the like.

At this time, the lower discharge of the distillation tower D2 was separated into a water layer and an organic layer, and 89% of the catalyst used in the esterification reaction was present in the water layer, which was then recirculated into the first esterification reactor R1.

Some (150 g/hr) of the organic layer was fed into a decomposition reactor for high boiling materials R3 while the rest of it was recirculated into the first esterification reactor R1. Also, the concentration of the catalyst in the decomposition reactor R3 was maintained at 2.8-3.0% by weight, for which the water layer separated from the lower discharge from the distillation tower D2 was intermittently supplied into the decomposition reactor R3.

The residence time in the decomposition reactor for high boiling materials R3 was 8 hours and the decomposition reaction proceeded at a temperature of 157° C. under a pressure of 100 Torr. The upper discharge from the decomposition reactor R3 came out at a flow rate of 126 g/hr and then it was recirculated into the first esterification reactor R1. Also, the lower discharge of the decomposition reactor R3 came out at a flow rate of 24 g/hr and the content of the organic acid catalyst therein was 2.9% by weight with respect to the total weight of the lower discharge.

Under the above conditions, the fluidity did not cause any problems in the decomposition reactor for high boiling materials R3 even when the process was operated for about 300 hours.

EXAMPLE 2

Butyl acrylate was prepared as a target alkyl (meth)acrylate.

For this, acrylic acid and n-butanol were used as starting materials, and p-toluene sulfonic acid and phenothiazine were used for a catalyst and a polymerization inhibitor, respectively. Also, for each of an esterification reactor and a distillation tower, a reboiler of the distillation tower, and a decomposition reactor for high boiling materials, the same apparatus was used as in Example 1.

345 g/hr of acrylic acid and 358 g/hr of n-butanol were fed into a first reactor R1 of the esterification reactors, respectively. As an organic acid catalyst, 0.75 g/hr of p-toluene sulfonic acid dissolved in n-butanol was continuously introduced. A mixed liquid comprising n-butanol, butyl acrylate, and water with the ratio of 7 (n-butanol):2 (butyl acrylate):1 (water) was fed into the upper part of a water separation tower D1 at a flow rate of 189 g/hr.

The esterification reaction proceeded such that the residence time of the reactants, the reaction temperature, and the reaction pressure in the first reactor R1 of the esterification reactors were 1.4 hours, 95° C. and 330 Torr, respectively; and the residence time of the reactants, the reaction temperature, and the reaction pressure in a second reactor R2 were 2.9 hours, 103° C. and 330 Torr, respectively. The content of the catalyst in the second reactor R2 was 1.01% by weight.

Subsequently, the reaction liquid discharged coming out from the second reactor R2 of the esterification reactors was introduced into the bottom of the distillation tower D2 wherein the pressure and the temperature of the upper part of the distillation tower D2 were 150 Torr and 54° C., respectively and the temperature of the liquid in the reboiler fitted to the lower end of the distillation tower was controlled to be 76° C.

Also, a refluxed liquid comprising 96.5% by weight of water and 3.5% by weight of n-butanol was fed from the upper part of the distillation tower D2 at a flow rate of 604 g/hr and at the same time, 1 0 butyl acrylate with 1.5% by weight of phenothiazine was introduced at a flow rate of 22 g/hr.

Meanwhile, 1315 g/hr of the upper discharge and 802 g/hr of the lower discharge came out from the distillation tower D2. The composition of the upper discharge from the distillation tower D2 was 48.5 (butyl acrylate):39.5 (water):12.0 (n-butanol) with acrylic acid being less then 1 ppm. In other words, the amount of the water supplied in the upper part of the distillation tower D2 (the converted value: 582.86 g/hr) was maintained to be about 1.12 times the amount of the water recovered from the upper part of the distillation tower in the recovery step (converted value: 519.425 g/hr).

Also, the lower discharge of the distillation tower D2 contained 10.1% by weight of water, 2.3% by weight of acrylic acid, 6.9% by weight of n-butanol, and 54% by weight of butyl acrylate, with the rest being heavies such as high boiling materials, the polymerization inhibitor, the catalyst and the like.

At this time, the lower discharge of the distillation tower D2 was separated into a water layer and an organic layer, and 78.3% of the catalyst used in the esterification reaction was present in the water layer, which was then recirculated into the first esterification reactor R1.

Some (158 g/hr) of the organic layer was fed into a decomposition reactor for high boiling materials R3 while the rest of it was recirculated into the first esterification reactor R1. Also, the concentration of the catalyst in the decomposition reactor R3 was maintained at 3.1% by weight, for which the water layer separated from the lower discharge from the distillation tower D2 was intermittently supplied into the decomposition reactor R3.

The residence time in the decomposition reactor for high boiling materials R3 was 8 hours and the decomposition reaction proceeded at a temperature of 157° C. under a pressure of 100 Torr. The upper discharge from the decomposition reactor R3 came out at a flow rate of 134 g/hr and then it was recirculated into the first esterification reactor R1. Also, the lower discharge of the decomposition reactor R3 came out at a flow rate of 24 g/hr and the content of the organic acid catalyst therein was 3.1% by weight with respect to the total weight of the lower discharge.

Under the above conditions, the fluidity did not cause any problems in the decomposition reactor for high boiling materials R3 even when the process was operated for about 300 hours.

EXAMPLE 3

Butyl acrylate was prepared as a target alkyl (meth)acrylate.

For this, acrylic acid and n-butanol were used as starting materials, and p-toluene sulfonic acid and phenothiazine were used for a catalyst and a polymerization inhibitor, respectively. Also, for each of an esterification reactor and a distillation tower, a reboiler of the distillation tower, and a decomposition reactor for high boiling materials, the same apparatus was used as in Example 1.

First, 348 g/hr of acrylic acid and 362 g/hr of n-butanol were fed into a first reactor R1 of the esterification reactors. As an organic acid catalyst, 0.83 g/hr of p-toluene sulfonic acid dissolved in n-butanol was continuously introduced. A mixed liquid comprising n-butanol, butyl acrylate, and water with the ratio of 7 (n-butanol):2 (butyl acrylate):1 (water) was fed into the upper part of a water separation tower D1 at a flow rate of 192 g/hr.

The esterification reaction proceeded such that the residence time of the reactants, the reaction temperature, and the reaction pressure in the first reactor R1 of the esterification reactors were 1.4 hours, 95° C. and 330 Torr, respectively; and the residence time of the reactants, the reaction temperature, and the reaction pressure in a second reactor R2 were 2.9 hours, 103° C. and 330 Torr, respectively. The content of the catalyst in the second reactor R2 was 1.1% by weight.

Subsequently, the reaction liquid discharged from the second reactor R2 of the esterification reactors was introduced into the bottom of the distillation tower D2 wherein the pressure and the temperature of the upper part of the distillation tower D2 were 190 Torr and 58.6° C., respectively and the temperature of the liquid in the reboiler fitted to the lower end of the distillation tower was controlled to be 87° C.

Also, a refluxed liquid comprising 96.5% by weight of water and 3.5% by weight of n-butanol was fed from the upper part of the distillation tower D2 at a flow rate of 611 g/hr and at the same time, butyl acrylate with 1.5% by weight of phenothiazine was introduced at a flow rate of 22 g/hr.

Meanwhile, 1331 g/hr of the upper discharge and 781 g/hr of the lower discharge came out from the distillation tower D2. The composition of the upper discharge from the distillation tower D2 was 48.5 (butyl acrylate):39.5 (water):12.0 (n-butanol) with acrylic acid being less then 1 ppm. In other words, the amount of the water supplied in the upper part of the distillation tower D2 (the converted value: 589.615 g/hr) was maintained to be about 1.12 times the amount of the water recovered from the upper part of the distillation tower in the recovery step (converted value: 525.745 g/hr).

Also, the lower discharge from the distillation tower D2 contained 6.5% by weight of water, 2.4% by weight of acrylic acid, 7.1% by weight of n-butanol, and 55% by weight of butyl acrylate, with the rest being heavies such as high boiling materials, the polymerization inhibitor, the catalyst and the like.

At this time, the lower discharge of the distillation tower D2 was separated into a water layer and an organic layer, and 83% of the catalyst used in the esterification reaction was present in the water layer, which was then recirculated into the first esterification reactor R1.

Some (154 g/hr) of the organic layer was fed into a decomposition reactor for high boiling materials R3 while the rest of it was recirculated into the first esterification reactor R1. Also, the concentration of the catalyst in the decomposition reactor R3 was maintained at 3.4% by weight, for which the water layer separated from the lower discharge from the distillation tower D2 was intermittently supplied into the decomposition reactor R3.

The residence time in the decomposition reactor for high boiling materials R3 was 8 hours and the decomposition reaction proceeded at a temperature of 157° C. under a pressure of 100 Torr. The upper discharge from the decomposition reactor R3 came out at a flow rate of 129 g/hr and then it was recirculated into the first esterification reactor R1. Also, the lower discharge of the decomposition reactor R3 came out at a flow rate of 24 g/hr and the content of the organic acid catalyst therein was 3.4% by weight with respect to the total weight of the lower discharge.

Under the above conditions, the fluidity did not cause any problems in the decomposition reactor for high boiling materials R3 even when the process was operated for about 300 hours.

[Explanation as to Reference Numerals]
R1 and R2: an esterification reactor
R3: a decomposition reactor for high boiling materials
D1: a water separation tower
D2: a distillation tower for esterification products
B: a reboiler of the distillation tower for esterification products
D3: a separation tower for low boiling materials
D4: a recovery tower for alcohols
T1, T2, and T4: a decanter and receiver
T3: a bath for recovering catalysts
1 to 3: supply lines for reactants and catalysts
4 to 22: lines for reaction products

The invention claimed is:

1. A method of preparing an alkyl (meth)acrylate which comprises the steps of:
carrying out an esterification reaction with reactants comprising an alkanol and (meth)acrylic acid in the presence of an organic acid catalyst with a conversion rate of 70% or more;
supplying reaction products of the esterification reaction to a distillation tower equipped with a reboiler at the lower end to purify them;
recovering a upper discharge comprising an alkyl (meth)acrylate and water at the upper part of the distillation tower and recovering a lower discharge comprising high boiling materials and water at the lower part of the distillation tower;
separating the lower discharge of the distillation tower into a water layer and an organic layer; and
recirculating the water layer separated from the lower discharge so as to be used in the esterification reaction,
wherein each of the steps occurs continuously
wherein the lower discharge of the distillation tower includes water in an amount of 2-25% by weight with respect to the total weight of the lower discharge, and
wherein the amount of water included in the lower discharge of the distillation tower is controlled by supplying water from the upper part of the distillation tower in an amount of 1.01-1.20 times the weight of the water included in the upper discharge coming out from the upper part of the distillation tower.

2. A method of preparing an alkyl (meth)acrylate which comprises the steps of:
carrying out an esterification reaction with reactants comprising an alkanol and (meth)acrylic acid in the presence of an organic acid catalyst with a conversion rate of 70% or more;
supplying reaction products of the esterification reaction to a distillation tower equipped with a reboiler at the lower end to purify them;
recovering a upper discharge comprising an alkyl (meth)acrylate and water at the upper part of the distillation tower and recovering a lower discharge comprising high boiling materials and water at the lower part of the distillation tower;
separating the lower discharge of the distillation tower into a water layer and an organic layer; and
recirculating the water layer separated from the lower discharge so as to be used in the esterification reaction,
wherein each of the steps occurs continuously,
wherein the lower discharge of the distillation tower includes water in an amount of 2-25% by weight with respect to the total weight of the lower discharge,
wherein the amount of water included in the lower discharge of the distillation tower is controlled by operating under such conditions that the pressure of the upper part of the distillation tower and the temperature of a liquid in the reboiler are at least 130 Torr but less than 170 Torr and 65-90° C., respectively; at least 170 Torr but less than 200 Torr and 70-95° C., respectively; or at least 200 Ton but less than 230 Torr and 75-100° C., respectively.

3. A method of preparing an alkyl (meth)acrylate which comprises the steps of:
carrying out an esterification reaction with reactants comprising an alkanol and (meth)acrylic acid in the presence of an organic acid catalyst with a conversion rate of 70% or more
supplying reaction products of the esterification reaction to a distillation tower equipped with a reboiler at the lower end to purify them;
recovering a upper discharge comprising an alkyl (meth)acrylate and water at the upper part of the distillation tower and recovering a lower discharge comprising high boiling materials and water at the lower part of the distillation tower;
separating the lower discharge of the distillation tower into a water layer and an organic layer; and
recirculating the water layer separated from the lower discharge so as to be used in the esterification reaction,
wherein each of the steps occurs continuously,
wherein the lower discharge of the distillation tower includes water in an amount of 2-25% by weight with respect to the total weight of the lower discharge,
wherein the amount of water included in the lower discharge of the distillation tower is controlled by operating under such conditions that the pressure of the upper part of the distillation tower and the temperature of a liquid in the reboiler are at least 130 Torr but less than 170 Torr and 65-90° C., respectively; at least 170 Torr but less than 200 Torr and 70-95° C., respectively; or at least 200 Torr but less than 230 Torr and 75-100° C., respectively; and further supplying water from the upper part of the distillation tower in an amount of 1.01-1.20 times the weight of the water included in the upper discharge coming out from the upper part of the distillation tower.

4. The method of preparing an alkyl (meth)acrylate according to claim 1, wherein the water layer separated from the lower discharge of the distillation tower includes at least 50% by weight of the organic acid catalyst supplied to the esterification reaction.

5. The method of preparing an alkyl (meth)acrylate according to claim 1, further comprising a step of supplying the organic layer separated from the lower discharge of the distillation tower to a decomposition reactor for high boiling materials to carry out a decomposition reaction.

6. The method of preparing an alkyl (meth)acrylate according to claim 5, wherein the decomposition reaction proceeds at a temperature of 120-220° C. under a pressure of 30-760 Torr.

7. The method of preparing an alkyl (meth)acrylate according to claim 5, further comprising a step of supplying a portion of the water layer separated from the lower discharge of the distillation tower into the decomposition reactor for high boiling materials.

8. The method of preparing an alkyl (meth)acrylate according to claim 7, wherein the catalyst contained in the decomposition reactor for high boiling materials can be in an amount of 0.01-5% by weight with respect to the total weight of reacting liquids fed into the decomposition reactor.

9. The method of preparing an alkyl (meth)acrylate according to claim 5, further comprising a step of recirculating the upper discharge of the decomposition reactor into the step of the esterification reaction.

10. The method of preparing an alkyl (meth)acrylate according to claim 5, further comprising a step of recirculating the upper discharge of the decomposition reactor into the step of purifying the reaction products of the esterification reaction.

11. The method of preparing an alkyl (meth)acrylate according to claim 5, wherein after the step of the decomposition reaction, the lower discharge of the decomposition reactor contains the catalyst in an amount of at most 10% by weight with respect to the total weight of the lower discharge.

12. The method of preparing an alkyl (meth)acrylate according to claim 1, wherein the esterification reaction proceed in at least one continuous type reactor connected in series.

13. The method of preparing an alkyl (meth)acrylate according to claim 12, wherein a water separation tower is further included for purifying water coming out from the upper part of each of the continuous type reactors.

14. The method of preparing an alkyl (meth)acrylate according to claim 1, wherein the esterification reaction proceeds at a temperature of 70-150° C. under a pressure of 50-760 Torr.

15. The method of preparing an alkyl (meth)acrylate according to claim 1, wherein a molar ratio of the alkanol to the (meth)acrylic acid included in the reactants of the step of the esterification reaction is 1 to 5.

16. The method of preparing an alkyl (meth)acrylate according to claim 1, wherein the content of the organic acid catalyst in the step of the esterification reaction is 0.01-5% by weight with respect to the total weight of the reactants.

17. The method of preparing an alkyl (meth)acrylate according to claim 1, wherein the alkanol is an alkanol having from 4 to 8 carbon atoms.

18. The method of preparing an alkyl (meth)acrylate according to claim 1, wherein the organic acid catalyst is at least one selected from the group consisting of alkane sulfonic acids and aryl sulfonic acids.

19. The method of preparing an alkyl (meth)acrylate according to claim 2, wherein the water layer separated from the lower discharge of the distillation tower includes at least 50% by weight of the organic acid catalyst supplied to the esterification reaction.

20. The method of preparing an alkyl (meth)acrylate according to claim 2, further comprising a step of supplying the organic layer separated from the lower discharge of the distillation tower to a decomposition reactor for high boiling materials to carry out a decomposition reaction.

21. The method of preparing an alkyl (meth)acrylate according to claim 2, wherein the esterification reaction proceed in at least one continuous type reactor connected in series.

22. The method of preparing an alkyl (meth)acrylate according to claim 2, wherein the esterification reaction proceeds at a temperature of 70-150° C. under a pressure of 50-760 Torr.

23. The method of preparing an alkyl (meth)acrylate according to claim 2, wherein a molar ratio of the alkanol to the (meth)acrylic acid included in the reactants of the step of the esterification reaction is 1 to 5.

24. The method of preparing an alkyl (meth)acrylate according to claim 2, wherein the content of the organic acid catalyst in the step of the esterification reaction is 0.01-5% by weight with respect to the total weight of the reactants.

25. The method of preparing an alkyl (meth)acrylate according to claim 2, wherein the alkanol is an alkanol having from 4 to 8 carbon atoms.

26. The method of preparing an alkyl (meth)acrylate according to claim 2, wherein the organic acid catalyst is at least one selected from the group consisting of alkane sulfonic acids and aryl sulfonic acids.

27. The method of preparing an alkyl (meth)acrylate according to claim 3, wherein the water layer separated from the lower discharge of the distillation tower includes at least 50% by weight of the organic acid catalyst supplied to the esterification reaction.

28. The method of preparing an alkyl (meth)acrylate according to claim 3, further comprising a step of supplying the organic layer separated from the lower discharge of the distillation tower to a decomposition reactor for high boiling materials to carry out a decomposition reaction.

29. The method of preparing an alkyl (meth)acrylate according to claim 3, wherein the esterification reaction proceed in at least one continuous type reactor connected in series.

30. The method of preparing an alkyl (meth)acrylate according to claim 3, wherein the esterification reaction proceeds at a temperature of 70-150° C. under a pressure of 50-760 Torr.

31. The method of preparing an alkyl (meth)acrylate according to claim 3, wherein a molar ratio of the alkanol to the (meth)acrylic acid included in the reactants of the step of the esterification reaction is 1 to 5.

32. The method of preparing an alkyl (meth)acrylate according to claim 3, wherein the content of the organic acid catalyst in the step of the esterification reaction is 0.01-5% by weight with respect to the total weight of the reactants.

33. The method of preparing an alkyl (meth)acrylate according to claim 3, wherein the alkanol is an alkanol having from 4 to 8 carbon atoms.

34. The method of preparing an alkyl (meth)acrylate according to claim 3, wherein the organic acid catalyst is at least one selected from the group consisting of alkane sulfonic acids and aryl sulfonic acids.

* * * * *